(12) United States Patent
Kim

(10) Patent No.: US 8,715,322 B2
(45) Date of Patent: May 6, 2014

(54) SPINE FIXATION DEVICE CONTAINING SET SCREW HAVING DOUBLE SPIRAL FORM

(75) Inventor: Min Seok Kim, Incheon (KR)

(73) Assignee: Min-Seok Kim, Incheon (KR)

( * ) Notice: Subject to any disclaimer, the term of this patent is extended or adjusted under 35 U.S.C. 154(b) by 0 days.

(21) Appl. No.: 13/318,136

(22) PCT Filed: Jul. 17, 2009

(86) PCT No.: PCT/KR2009/003962
§ 371 (c)(1),
(2), (4) Date: Apr. 4, 2012

(87) PCT Pub. No.: WO2010/126201
PCT Pub. Date: Nov. 4, 2010

(65) Prior Publication Data
US 2013/0018420 A1  Jan. 17, 2013

(30) Foreign Application Priority Data

Apr. 30, 2009  (KR) .................. 10-2009-0038346

(51) Int. Cl.
*A61B 17/70* (2006.01)
(52) U.S. Cl.
USPC ........... 606/264; 606/275; 606/300; 606/301; 606/317
(58) Field of Classification Search
USPC .......... 606/246, 264–278, 300–321; 411/307, 411/308, 412, 413, 415
See application file for complete search history.

(56) References Cited

U.S. PATENT DOCUMENTS

| | | | |
|---|---|---|---|
| 5,190,426 A * | 3/1993 | Wieder et al. | 411/412 |
| 2004/0082956 A1 * | 4/2004 | Baldwin et al. | 606/73 |
| 2010/0094353 A1 * | 4/2010 | Shim et al. | 606/301 |

* cited by examiner

*Primary Examiner* — Mary Hoffman
*Assistant Examiner* — Christina Negrellirodriguez
(74) *Attorney, Agent, or Firm* — TIPS Group

(57) ABSTRACT

The present invention relates to a spine fixation device containing a set screw having a double spiral form. The spine fixation device is characterized by comprising: a pedicle fixation screw which has a head portion having a receiving groove of a certain depth formed thereinside and a plurality of female screws formed in one region of the inner circumference of the receiving groove, and a screw portion extended from one side of the head portion lengthwise and embedded into a pedicle, and is fixed to a damaged pedicle; a spine rod which is received in the receiving groove to connect the pedicle fixation screw, thereby realigning the angle and interval of the pedicle; and a set screw which forms a plurality of male screws with the same screw inner diameter, the same screw thread direction and different pitches, and is screw-coupled to the female screws of the pedicle fixation screw to prevent the movement of the rod received in the receiving groove. Therefore, the fastening force of the pedicle fixation screw and the set screw is increased, the movement of the spine rod is prevented in case of the realignment of the pedicle, and a spine can be realigned stably.

1 Claim, 5 Drawing Sheets

SPINE FIXATION DEVICE CONTAINING SET SCREW HAVING DOUBLE SPIRAL FORM

CROSS REFERENCE TO RELATED APPLICATIONS

This application claims the priority of International Application PCT/KR2009/003962, filed Jul. 17, 2009, which claims the priority of Korean application number 10-2009-0038346, filed Apr. 30, 2009, both of which are incorporated herein by reference.

TECHNICAL FIELD

The present invention relates to a spine fixation device containing a set screw having a double spiral form, and more specifically to a spine fixation device containing a set screw having a double spiral form with an improved screw fastening structure of a pedicle fixation screw and set screw.

BACKGROUND ART

The human spine consists of 24 bones, which are engaged with each other in joint forms and can support the axial load even in a bent condition. A plurality of discs are arranged between bones to function as a buffer.

The spine has a structure of various names according to the anatomical profile, and in general it has a form bent in an "S" letter shape.

Spinal diseases are caused by impact to the spine by repeatedly applied loads, the decrease of spinal motility due to aging, and the degeneration of the spine itself.

At this time, a frequent and representative symptom of a patient suffering from spinal stenosis is a pain caused by pressed nerves which came out to left or right between bones due to the damage to the disc.

A patient with a spine partly damaged as described above cannot perform activities necessary for his personal life under such a condition, and even if the extent of damage is not so severe, the damaged part of the spine may be pressed or touched by other adjacent parts to cause pain.

So in the case of a patient with part of the spine damaged or injured, an artificial aid should be used in the operation for supporting the adjacent portion of the spine so that the damaged part is not pressed or compressed.

At this time, the artificial aid used for supporting the spine consists of pedicle fixation screws, which are inserted into the top and bottom sides of the damaged spine for a support role, and a spinal rod, which is connected through the pedicle fixation screw for an orthotic role.

The pedicle fixation screws that are inserted into the pedicle structure with the best bone density according to spinal motility can be inserted through several segments of pedicle.

The spinal rod which is fixed in the head portion of the pedicle fixation screws has an anatomical curve that a spinal segment has, and is used for connecting the pedicle fixation screws.

Also, the set screw that fixes the spinal rod to the pedicle fixation screws is a fastening element which converts angular motion into linear motion or inversely by the screw fastening method. Namely, the set screw, which is one of mechanical fastening elements, is a screw for motion that receives large axial force with small angular moment.

Meanwhile, the set screw that fixes and fastens the spinal rod to the pedicle fixation screws should prevent the spinal rod from sliding or detaching.

In the conventional spine fixation device, when joining the male screw of the set screw to the female screw of the pedicle fixation screw, the screw thread surface of the male screw of the set screw does not completely contact the screw thread surface of the female screw of the pedicle fixation screw. Because of that, there occurs a gap between the screw thread surface of the male screw of the set screw and the screw thread surface of the female screw of the pedicle fixation screw, so there is a limit to maintenance of self-locking.

Therefore, in the conventional spine fixation device, the fastening force is decreased as the screws are loosened due to the limit of self-locking between the pedicle fixation screw and the set screw when correcting the pedicle. Accordingly, there is a problem that the spine cannot be stably corrected because the movement of the spinal rod increases.

DISCLOSURE

Technical Problem

Accordingly, it is an object of the present invention to provide a spinal fixation device containing a set screw having a double spiral form which enhances the fastening force of the pedicle fixation screw and the set screw, and prevents the movement of the spinal rod when correcting the pedicle, so that the spine can be corrected stably.

Technical Solution

In order to accomplish the foregoing objects, according to an embodiment of the present invention, there is provided a spine fixation device including a set screw having a double spiral form comprising: a pedicle fixation screw which has a head portion having a receiving groove with a certain depth formed therein and a plurality of female screws formed in one region of the inner circumference of the receiving groove, and a screw portion which is extended lengthwise from one side of the head portion to be embedded into a pedicle and is fixed to a damaged pedicle; a spinal rod which is received in the receiving groove to connect the pedicle fixation screws, thereby realigning the angle and interval of the pedicle; and a set screw in which a plurality of male screws having the same screw inner diameter, the same screw thread direction and different pitches are formed, and which is screw-coupled to the female screw of the pedicle fixation screw to prevent the movement of the rod received in the receiving groove.

In the present invention, the set screw includes a first male screw portion in which a plurality of male screws having a first pitch identical to the female screw of the pedicle fixation screw are formed, and a second male screw portion in which a plurality of male screws having a second pitch different from the first pitch are formed.

Preferably, the second male screw portion is formed on an outer circumference extended lengthwise from one end of the first male screw portion.

According to another embodiment of the present invention, the first male screw portion and the second male screw portion may be alternately provided in a lengthwise direction of the set screw.

Preferably, the second pitch has a size 1/n times the first pitch, wherein n is a natural number of 2 or more.

Advantageous Effects

According to the present invention, by improving the screw fastening structure of the pedicle fixation screw and the set screw, the fastening force of the pedicle fixation screw and the set screw is increased, and the movement of the spinal rod is prevented when correcting the pedicle, so that the spine can be stably corrected.

BRIEF DESCRIPTION OF THE DRAWINGS

The above objects, features and advantages of the present invention will become more apparent to those skilled in the related art in conjunction with the accompanying drawings. In the drawings.

DESCRIPTION OF REFERENCE NUMERALS IN DRAWINGS

Figure 1:
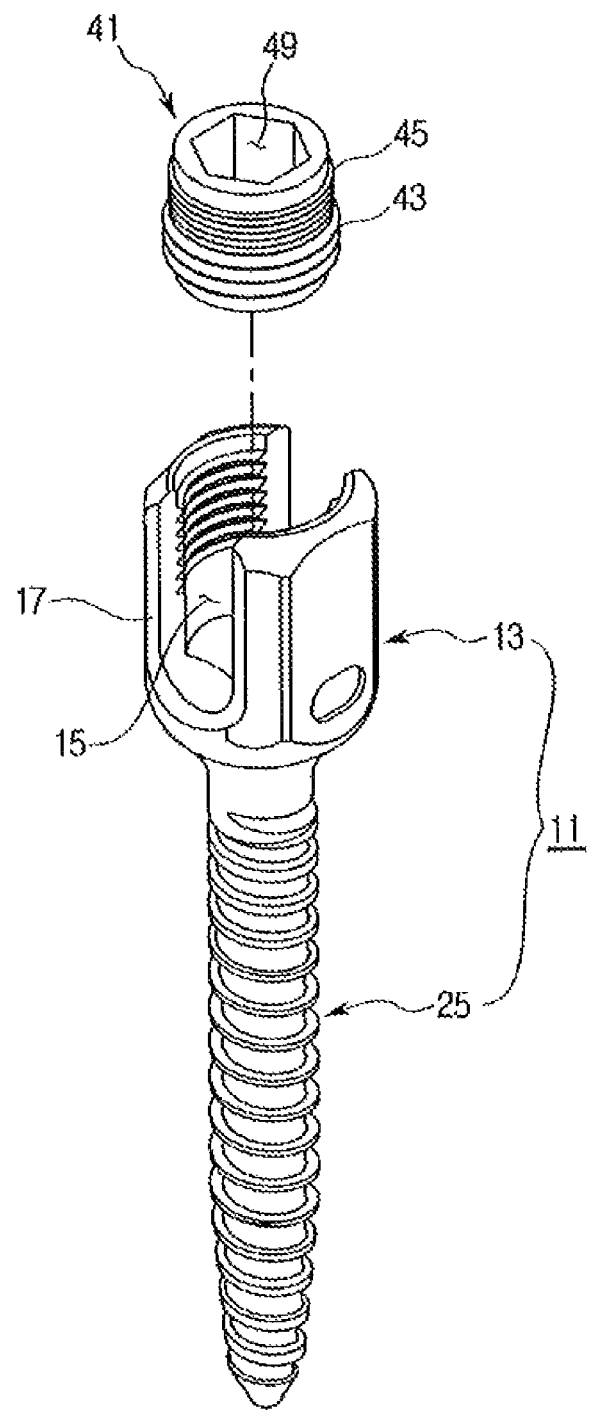
FIG. 1 is an exploded perspective view of a spine fixation device according to the present invention.
Figure 2:
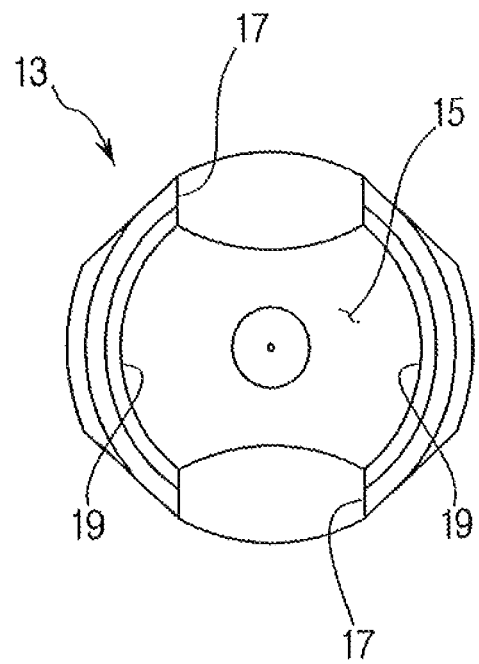
FIG. 2 is a plan view of the pedicle fixation screw shown in FIG. 1.

11: Pedicle fixation screw, 13: Head portion
15: Receiving groove, 17: Cut portion
19: Female screw, 25: Screw portion
31: Spinal rod, 41: Set screw
43: First male screw portion, 45: Second male screw portion
47: Elastically deformed portion, 49: Tool mounting slot
P1: First pitch, P2: Second pitch

DETAILED DESCRIPTION OF THE INVENTION

Hereinafter, exemplary embodiments of the present invention will be described in detail below with reference to the accompanying drawings.

FIGS. 1 to 5 illustrate a pedicle fixation screw containing a set screw having a spiral form according to the present invention. As shown in these drawings, the pedicle fixation screw containing a set screw having a spiral form according to the present invention includes a pedicle fixation screw 11, a spinal rod 31 which connects a plurality of the pedicle fixation screws 11 to realign the angle and interval of the pedicle, and a set screw 41 which is screw-coupled to the pedicle fixation screw 11.

The pedicle fixation screw 11 has a head portion 13 in which a receiving groove 15 with a certain depth is formed, and a screw portion 25 which is extended lengthwise from one side of the head portion 13.

A pair of cut portions 17 are formed in the head portion 13 so that the spinal rod 31 can be easily received in the receiving groove 15 of the pedicle fixation screw 11, and these cut portions 17 are cut lengthwise of the pedicle fixation screw 11. The head portion 13 has a generally "U" shaped section form as seen from the side. It is preferable that the bottom of the receiving groove 15 of the head portion 13 has a partially circular arc shape having a radius of curvature corresponding to the sectional shape of the spinal rod 31.

A plurality of female screws 19 are formed on the upper inner circumference of the head portion 13, and the set screw 41 is screw-coupled to the plurality of female screws 19. Each female screw 19 of the head portion 13 has a triangular screw shape, and the interval of the screw threads of the female screws 19 has a first pitch P1.

Also, the outer circumference of the head portion 13 has a polygonal section shape unlike the conventional circular section shape. Therefore, since the cross-sectional secondary moment of the head portion 13 of the pedicle fixation screw 11 becomes smaller than that of the conventional pedicle fixation screw, the deformation of the head portion 13, which is caused by the axial force due to the angular moment following the screw fastening of the head portion 13 and the set screw 41 and the force contrary to this is, minimized. As a result, it is possible to provide a strong fastening force between the head portion 13 and the set screw 41.

The screw portion 25 has a certain length, and triangular screws of a certain specification are formed on the outer circumference of the screw portion 25. The screw portion 25 is embedded into a certain depth in the vertical direction of the pedicle to play a support role of the damaged pedicle.

A bar-shaped spinal rod 31 has a circular section, and is received in the receiving groove 15 of the head portion 13 to connect the pedicle fixation screws 11, and also realigns the angle and interval of the pedicle.

Figure 3:
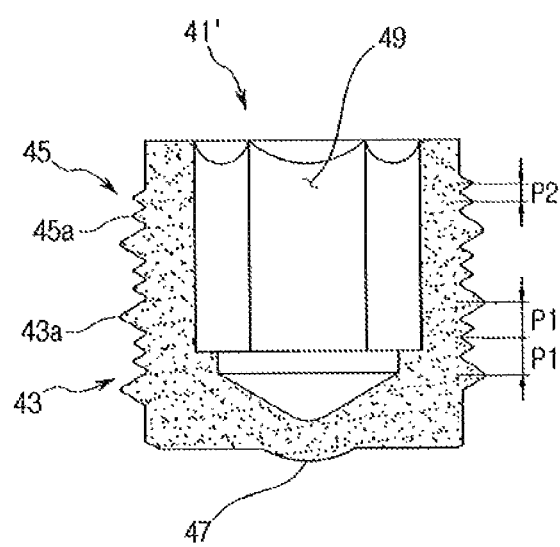
FIG. 3 is a sectional view of the set screw shown in FIG. 1.
Figure 4:
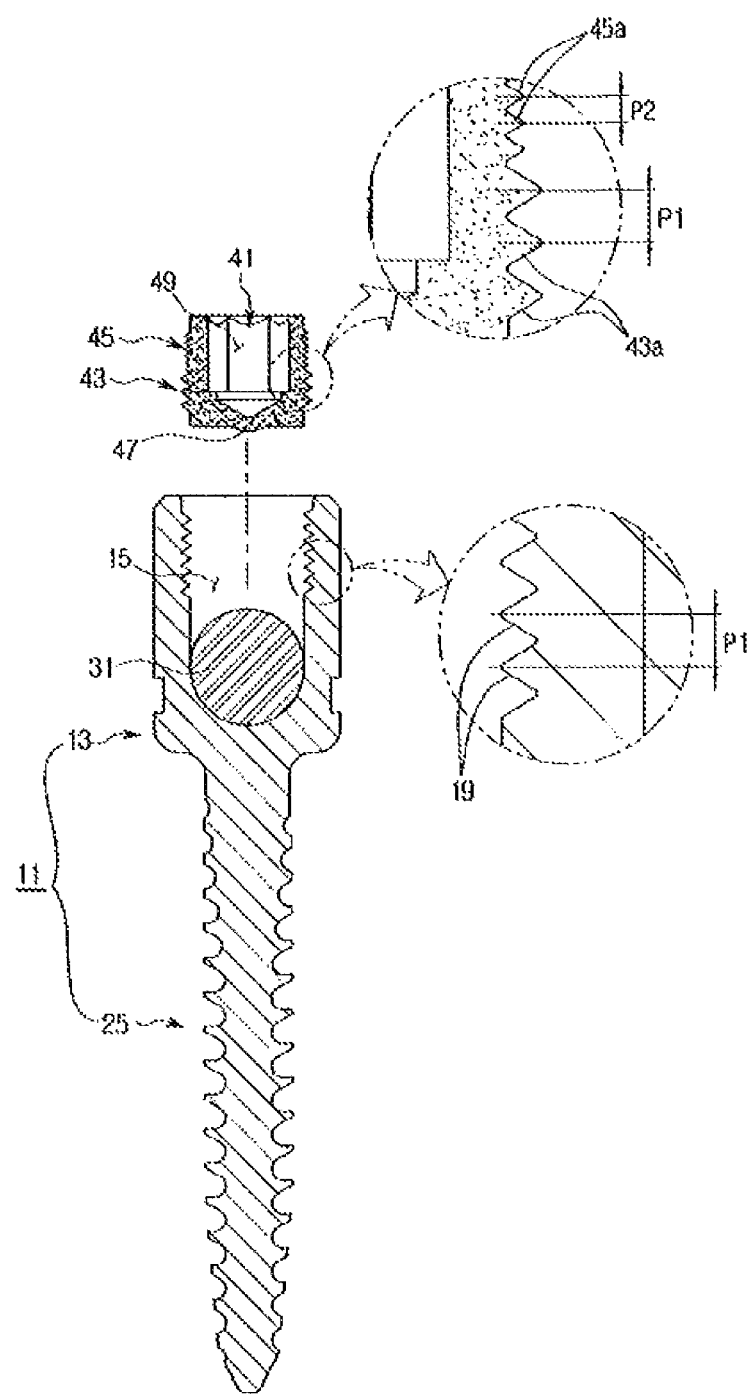
FIG. 4 is a sectional view illustrating the state that the set screw is separated from the pedicle fixation screw of the spine fixation device according to the present invention.

A bar-shaped set screw 41 has a certain length, and as shown in FIG. 3, a plurality of male screws 43a and 45a having different pitches are formed on the outer circumference of the set screw 41. On the outer circumference of one region of the set screw 41 is provided a first male screw portion 43 on which a plurality of male screws 43a having the first pitch P1 are formed, and on the outer circumference of the other region of the set screw 41 is provided a second male screw portion 45 on which a plurality of male screws 45a having the second pitch P2 different from the first pitch P1 of the first male screw portion 43 are formed. The male screws 43a and 45a of the first male screw portion 43 and the second male screw portion 45 are formed of triangular screws, and the screw inner diameter and the screw thread direction are identical.

Meanwhile, the second pitch P2 of the second male screw portion 45 of the set screw 41 has a relatively small size compared to the first pitch P1 of the first male screw portion 43, that is, it has a size 1/n times the first pitch P1. Here, n is preferably a natural number of 2 or more. In the present embodiment, the second pitch P2 of the second male screw portion 45 has a size ½ (0.5) times the first pitch 1 of the first male screw portion 43.

The front end of the first male screw portion 43 of the set screw 41 opposing the spinal rod 31 is provided with an elastically deformed portion 47 which is elastically deformed in the opposite direction of screw tightening of the set screw 41 as the spinal rod 31 is pressed. Inside the set screw 41 is formed to a certain depth a tool mounting slot 49 into which a tool such as a wrench for joining or separation of the set screw 41 to or from the pedicle fixation screw 11 is inserted.

The tool mounting slot 49 is formed in depression to a certain depth lengthwise of the screw 41 so that the elastically deformed portion 47 has an elastically deformable depth.

By dint of such a construction, below will be described the process of using the spine fixation device including the set screw having a double spiral form according to the present invention.

First, fix the pedicle fixation screw 11 to the pedicle. Next, insert the spinal rod 31 simultaneously into the receiving grooves 15 of a plurality of pedicle fixation screws 11 to be connected.

And, fasten the set screw 41 to the head portion 13 of the pedicle fixation screw 11, with the first male screw portion 43 of the set screw 41 facing the spinal rod 31, so that the spinal rod 31 is contacted with the bottom of the receiving groove 15 of the head portion 13 without movement.

Figure 5:
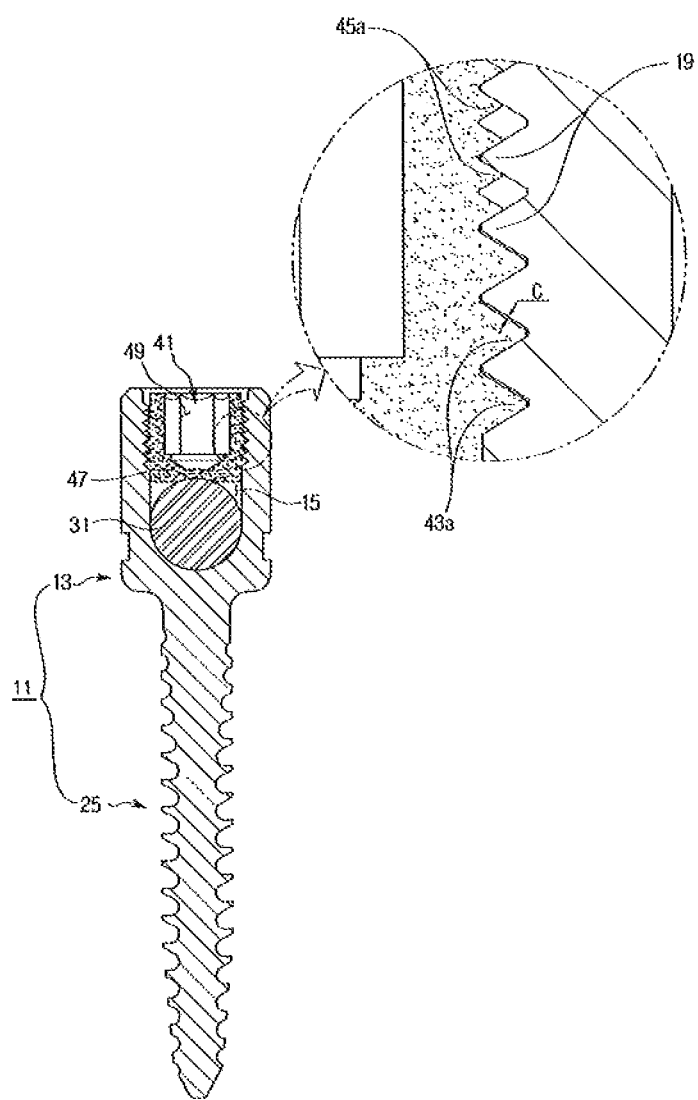
FIG. 5 is a sectional view illustrating the state that the set screw is mounted on the head portion of the pedicle fixation screw of the spine fixation device according to the present invention.

When screw-coupling the first male screw portion 43 of the set screw 41 to the female screw 19 of the pedicle fixation screw 11, the screw thread surface of the male screw 43a of the first male screw portion 43 facing the spinal rod 31 is completely contacted with the screw thread surface of the female screw 19 of the pedicle fixation screw 11, as shown in FIG. 5. At this time, there occurs a gap C between the screw thread surface of the male screw 43a of the first male screw portion 43 facing the opposite side of the spinal rod 31 and the screw thread surface of the female screw 19 of the pedicle fixation screw 11.

Also, a pair of male screws 45a of the second male screw portion 45 of the set screw 41 are positioned between a pair of female screws 19 of the pedicle fixation screw 11, and there occur no gaps between the screw thread surfaces of a pair of male screws 45a of the second male screw portion 45 facing the screw thread surfaces of a pair of female screws 19 of the pedicle fixation screw 11 and the screw thread surfaces of a pair of female screws 19. Therefore, the contact area between the female screw 19 of the pedicle fixation screw 11 and the male screw 45a of the second male screw portion 45 increases, which results in the increase in the fastening force of the pedicle fixation screw 11 and the set screw 41 after screw-coupling.

And, if the elastically deformed portion 47 of the set screw 41 presses the spinal rod 31 by means of the screw tightening force more than a certain amount; the elastically deformed portion 47 is contacted with one region of the outer circumference of the spinal rod 31. By dint of that, the elastically deformed portion is elastically deformed in the opposite direction of the screw tightening of the set screw 41. Therefore, the female screw 19 of the head portion 13 is prevented from being deformed by the tightening force of the set screw 41, so that the male screw portions 43 and 45 of the set screw 41 stably maintain screw-coupling with the female screw 19 of the head portion 13 and the fastening force is increased.

Figure 6:
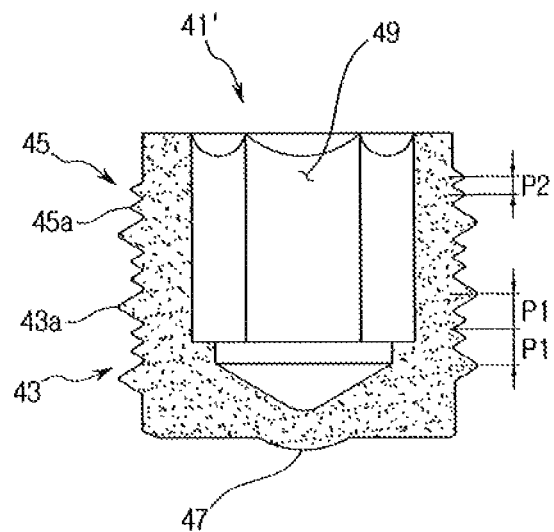
FIG. 6 is a sectional view of the set screw of a pedicle fixation device according to another embodiment of the present invention.
Figure 7:
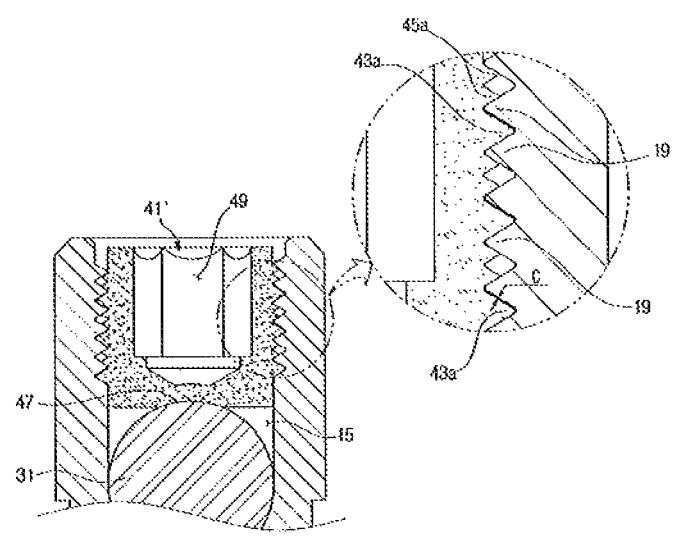
FIG. 7 is an enlarged sectional view of a major part illustrating the state that the set screw shown in FIG. 6 is mounted on the head portion of the pedicle fixation screw.

Meanwhile, in another embodiment shown in FIG. 6 of the set screw of the spine fixation device including a set screw having a double spiral form according to the present invention, a first male screw portion 43 and a second male screw portion 45 are alternately provided in a lengthwise direction of the set screw 41'. Namely, one male screw 43a of the first male screw portion 43 and a pair of male screws 45a of the second male screw portion 45 are alternately provided in a lengthwise direction of the set screw 41'.

If such a set screw 41' is screw-coupled to the pedicle fixation screw 11, there will be no gaps between the screw thread surfaces of a pair of male screws 45a of the second male screw portion 45 facing the screw thread surfaces of a pair of female screws 19 of the pedicle fixation screw 11 and the screw thread surfaces of a pair of the female screws 19 of the pedicle fixation screw 11, as mentioned above. Therefore, after screw-coupling, the fastening force of the pedicle fixation screw 11 and the set screw 41' can be increased.

Thus, according to the present invention, by screw-coupling the set screw in which a plurality of male screws having the same screw inner diameter, the same screw thread direction and different pitches to the female screw of the pedicle fixation screw, the fastening force of the pedicle fixation screw and the set screw is increased to prevent the pedicle fixation screw and the set screw from being released easily by external force. Therefore, the spine can be stably corrected by preventing the movement of the spinal rod when correcting the pedicle.

Although the present invention has been described in connection with the exemplary embodiments illustrated in the drawings, it is only illustrative. It will be understood by those skilled in the art that various modifications and equivalents can be made to the present invention. Therefore, the true technical scope of the present invention should be defined by the appended claims.

What is claimed is:

1. A spine fixation device containing a set screw having a double spiral form comprising:
    a pedicle fixation screw which has a head portion having a receiving groove with a certain depth formed therein and a plurality of female screws formed in one region of the inner circumference of the receiving groove, and a screw portion which is extended lengthwise from one side of the head portion to be embedded into a pedicle and is fixed to a damaged pedicle;
    a spinal rod which is received in the receiving groove to connect pedicle fixation screws, thereby realigning the angle and interval of the pedicle; and
    a set screw in which a plurality of male screws having the same screw inner diameter, the same screw thread direction and different pitches are formed, and which is screw-coupled to the plurality of female screws of the pedicle fixation screw to prevent movement of the rod received in the receiving groove;
    wherein the set screw includes:
        a first male screw portion in which a plurality of male screws having a first pitch the same pitch as the plurality of female screws of the pedicle fixation screw are formed; and
        a second male screw portion in which a plurality of male screws having a second pitch being smaller than the first pitch are formed and which has a smaller outer diameter than the inner diameter of the plurality of female screws; and
    wherein the first male screw portion is connected to the second male screw portion, and the number of male screws of the second male screw portion is n and the second pitch has a size 1/n times the first pitch, wherein n is a natural number of 2 or more.

* * * * *